Jan. 18, 1938. F. H. HOWARD Plant Pat. 268
ROSE
Filed Jan. 5, 1937
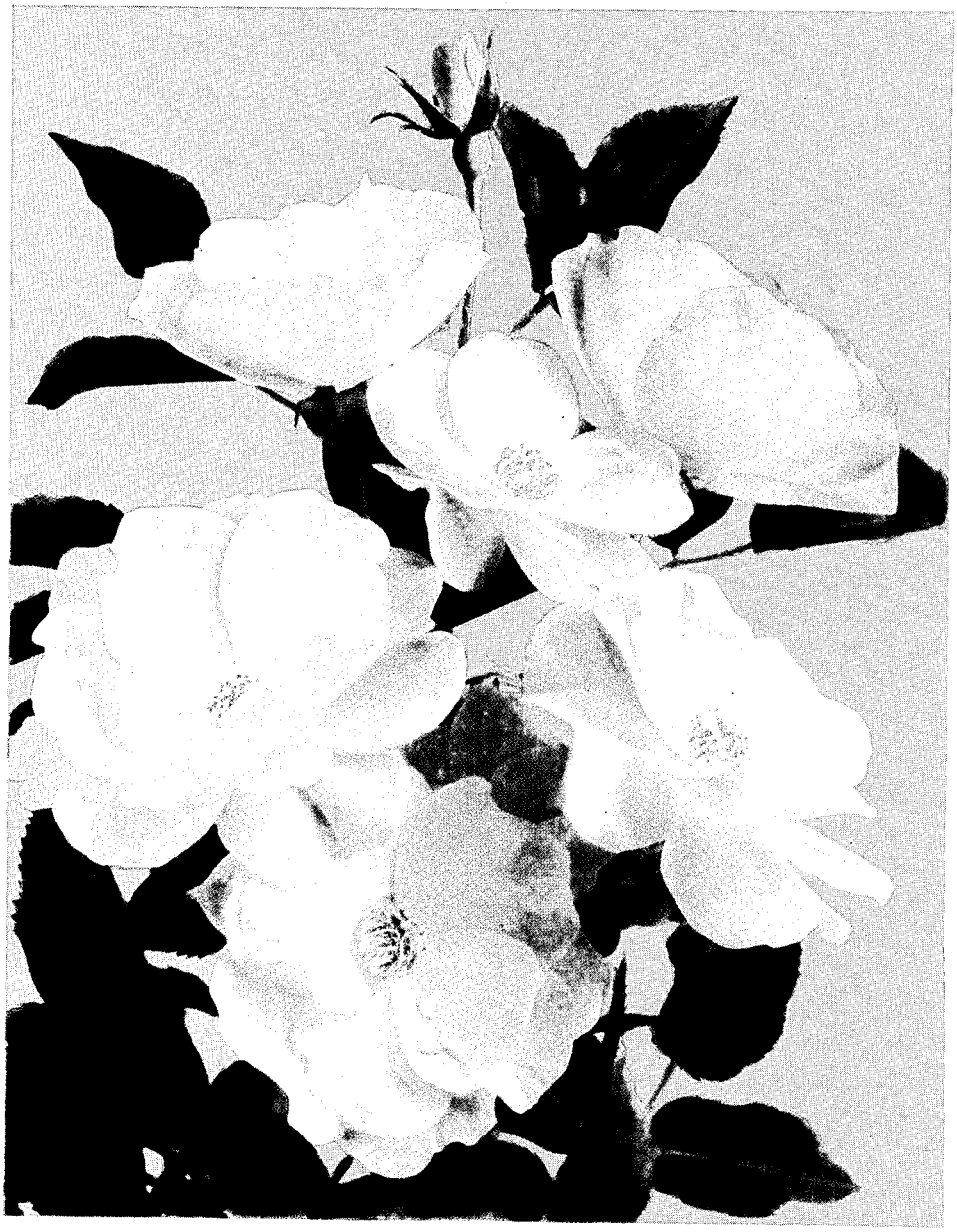
INVENTOR
Frederick Huber Howard
By Orville M. Kile
Plant Patent Agent.

Patented Jan. 18, 1938

Plant Pat. 268

UNITED STATES PATENT OFFICE

268

ROSE

Frederick Huber Howard, Montebello, Calif.

Application January 5, 1937, Serial No. 119,146

1 Claim. (Cl. 47—61)

My present invention relates to a new and distinct variety of rose plant of a type intermediate between the polyantha and the Hybride tea classes. It is the result of definite breeding efforts by the inventor and is the result of a cross between Rowena Thom and an unnamed seedling.

This new variety of rose is of particular value for use as a forcing variety for pot work because of the excellent lasting and keeping qualities of its blossoms on the bush, its ever-blooming quality, and other desirable qualities mentioned herein. However it is also a consistent producer when planted in beds in the open garden.

The distinguishing characters of this new variety have held throughout the asexual reproduction of several generations.

The accompanying illustrations show a cluster of flowers, together with foliage, in approximately natural size and color. Following is a more complete description of the plant and flower of this new variety.

*The plant*

*Growth habits.*—Low, spreading bush form—reaching about two feet in height. A constant, prolific bloomer. Many branches. Flowers borne in clusters of from three to ten.

*Disease resistance.*—Practically immune to mildew.

*Stems.*—Rigid; deep green; thorns moderate number.

*Nodes.*—Close set.

*Peduncle.*—One and one-half to two inches in length; slightly spined; same color as stem.

*Foliage.*—Small but plentiful; glossy.

*Leaves.*—Compound, consisting of from 3 to 7 leaflets; leathery texture; margin sharply but not deeply serrated. Terminal leaflet is about one-third larger than lateral ones in same group. Terminal leaflets are long and pointed, averaging 1½ inches long by 1 inch wide.

*Color.*—Upper leaf area bright glossy green; reverse side light green devoid of glossiness.

*Rachis.*—Slightly grooved with under side moderately fine spined.

*Stipules.*—Short; somewhat narrow.

*Sepals.*—Rather short.

*The flower*

*Bud:*

*Form.*—Short, conical polyantha type.

*Color.*—Deep Rose Pink (Plate XII, Ridgway's Color Standards and Nomenclature).

*Opening.*—Quick, but uniformly even.

*Bloom:*

*Form.*—Saucer-shaped and convolute when fully developed.

*Size.*—Three to three and one-half inches across; stamens and pistils fully exposed in developed flower.

*Petalage.*—Semi-double, averaging about ten petals under southern California climatic conditions.

*Petals.*—Thick and leathery; evenly arranged and of nearly equivalent size.

*Behavior.*—Tenacious until flower dies, at which time they drop cleanly.

*Shape.*—Somewhat obovate; slightly wavy at edges.

*Color.*—Under and upper surfaces uniform clear pink, merging into white at the base of the petals. This pink color might popularly be called appleblossom pink. The color is not shown by Ridgway's but would be similar to a color between Rose Pink and Deep Rose Pink (Plate XII).

*General color effect.*—A clear appleblossom pink which is retained until the flowers die; nonfading.

*Keeping qualities.*—Very lasting on bush, remaining in truss for eight to ten days.

*Fragrance.*—Slight fruit scent.

*Reproductive organs:*

*Stamens.*—Very numerous; uneven in arrangement.

*Filaments.*—Both long and short ones.

*Anthers.*—Dark brown.

*Pollen.*—Plentiful.

*Pistils.*—Moderate in number; close set.

*Styles.*—Uneven; short; white; hirsute.

*Stigma.*—White, tinged green.

*Ovaries.*—Enclosed in calyx.

*Hips.*—Very small; smooth; glossy green.

Having thus disclosed my invention, what I claim is:

A new and distinct variety of rose plant as herein described and shown, characterized particularly by its constant production of bloom, its glossy foliage, its apparent immunity to mildew, and its semi-double blossoms of excellent lasting qualities and distinct clear pink color as described and shown.

FREDERICK HUBER HOWARD.